United States Patent [19]

Su

[11] Patent Number: 5,430,185
[45] Date of Patent: Jul. 4, 1995

[54] PROCESS FOR MANUFACTURING CRYSTALLINE CALCIUM MAGNESIUM ACETATE

[75] Inventor: Fu Su, Hercules, Calif.

[73] Assignee: General Atomics International Services Corporation, San Diego, Calif.

[21] Appl. No.: 839,033

[22] Filed: Feb. 18, 1992

Related U.S. Application Data

[63] Continuation of Ser. No. 431,915, Nov. 6, 1989, abandoned, which is a continuation-in-part of Ser. No. 360,369, Jun. 2, 1989, abandoned.

[51] Int. Cl.⁶ .................... C07C 53/08; C07C 51/42; C09K 3/18
[52] U.S. Cl. .................... 562/607; 562/606; 562/608; 427/220; 428/403; 252/70
[58] Field of Search .................... 562/606, 607, 608; 427/220; 428/403; 252/70

[56] References Cited

U.S. PATENT DOCUMENTS

| | | |
|---|---|---|
| 4,389,323 | 6/1983 | Gancy .................... 562/607 X |
| 4,426,308 | 1/1984 | Gancy .................... 562/607 X |
| 4,606,836 | 8/1986 | Gancy .................... 562/607 X |
| 4,699,725 | 10/1987 | Gancy .................... 562/607 X |
| 4,913,831 | 4/1990 | Todd, Jr. et al. .................... 562/607 X |

*Primary Examiner*—Arthur C. Prescott
*Attorney, Agent, or Firm*—Reginald J. Suyat

[57] ABSTRACT

A process is provided for making bulk calcium magnesium acetate in a substantially pure crystalline form. The crystalline CMA contains less than about 0.5% of water soluble impurities.

28 Claims, 15 Drawing Sheets

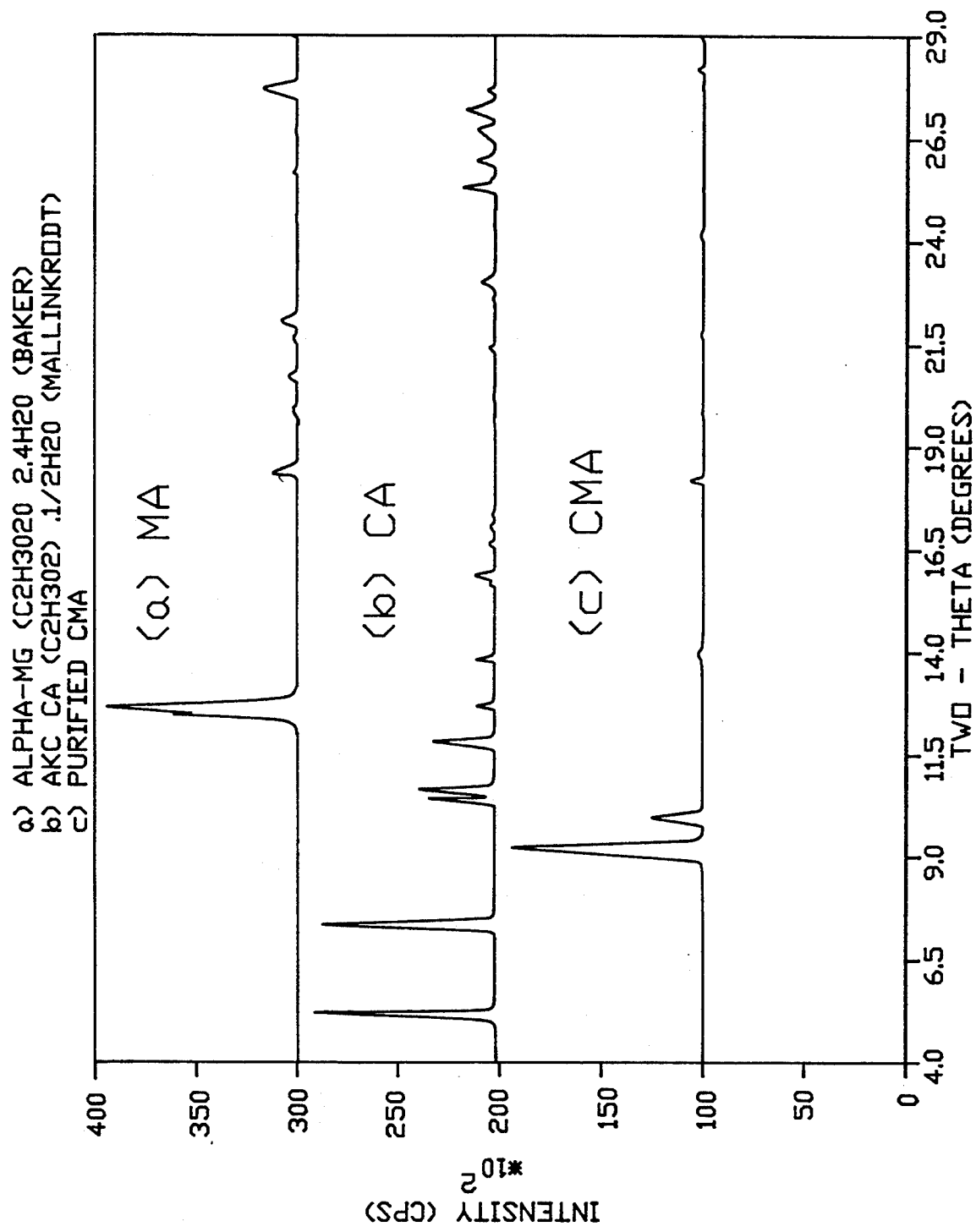

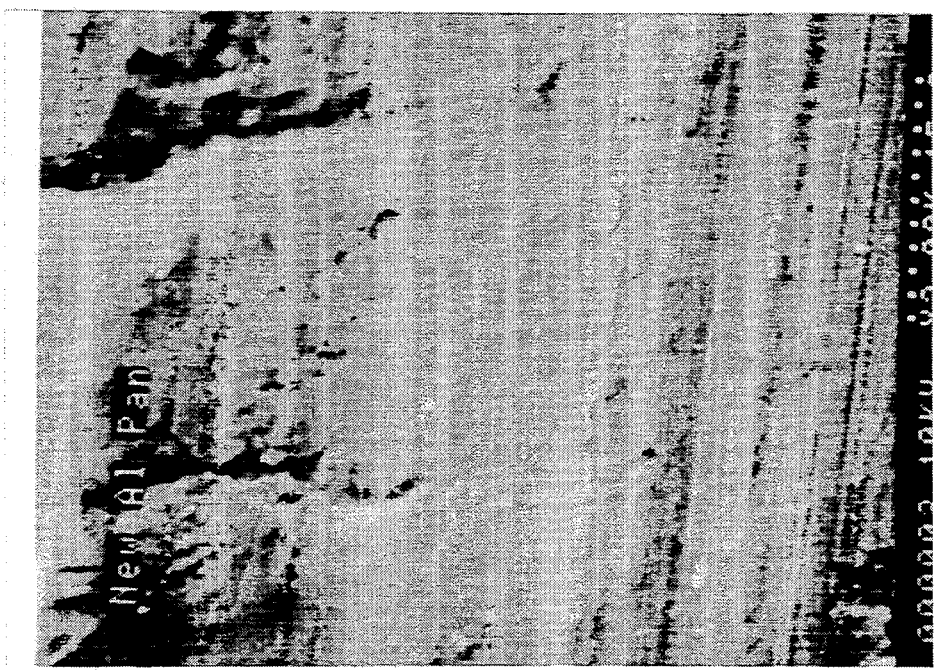
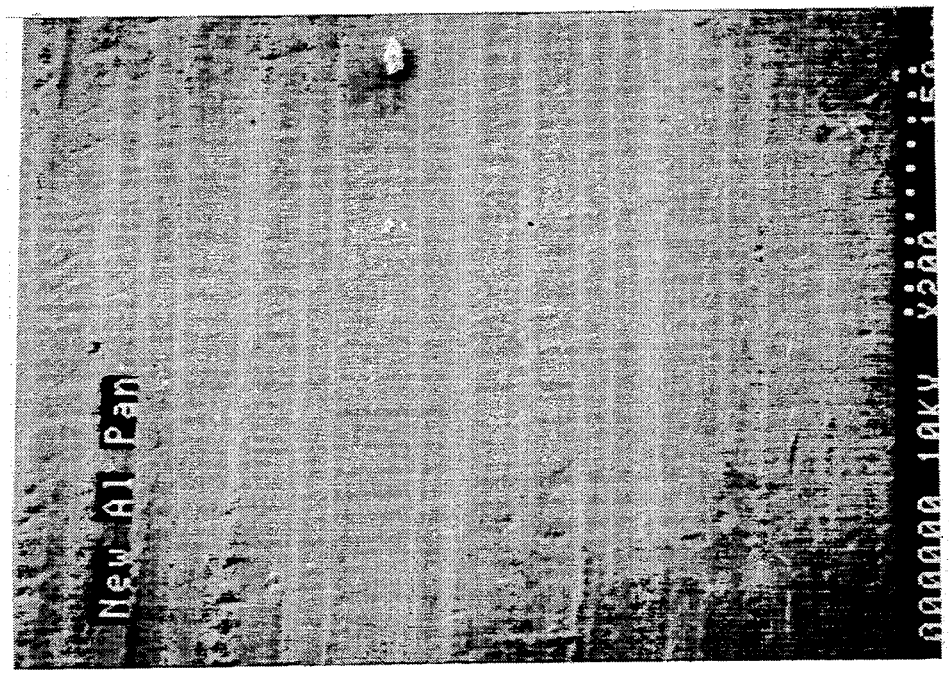
FIG. 4.

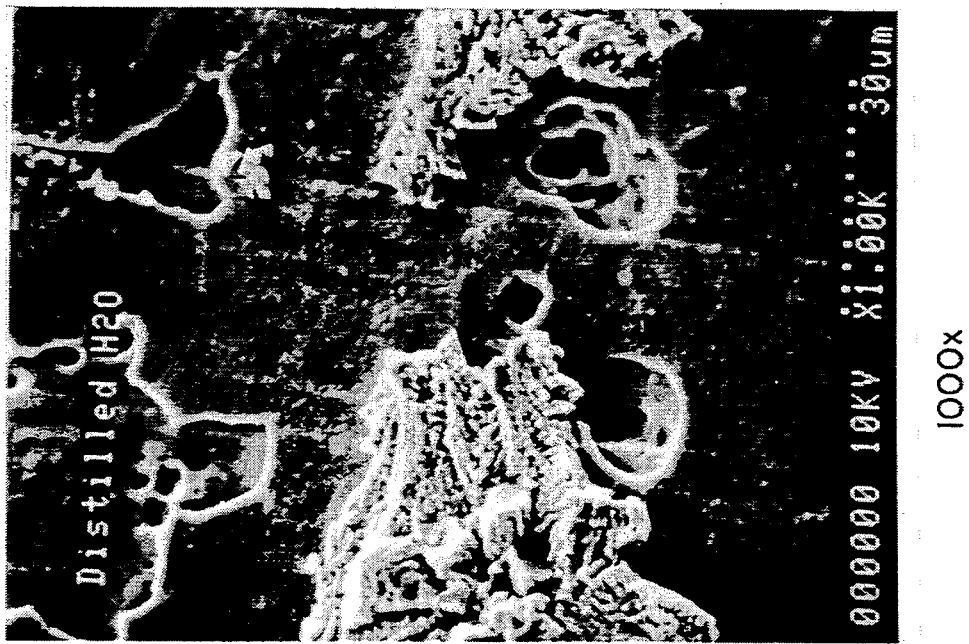
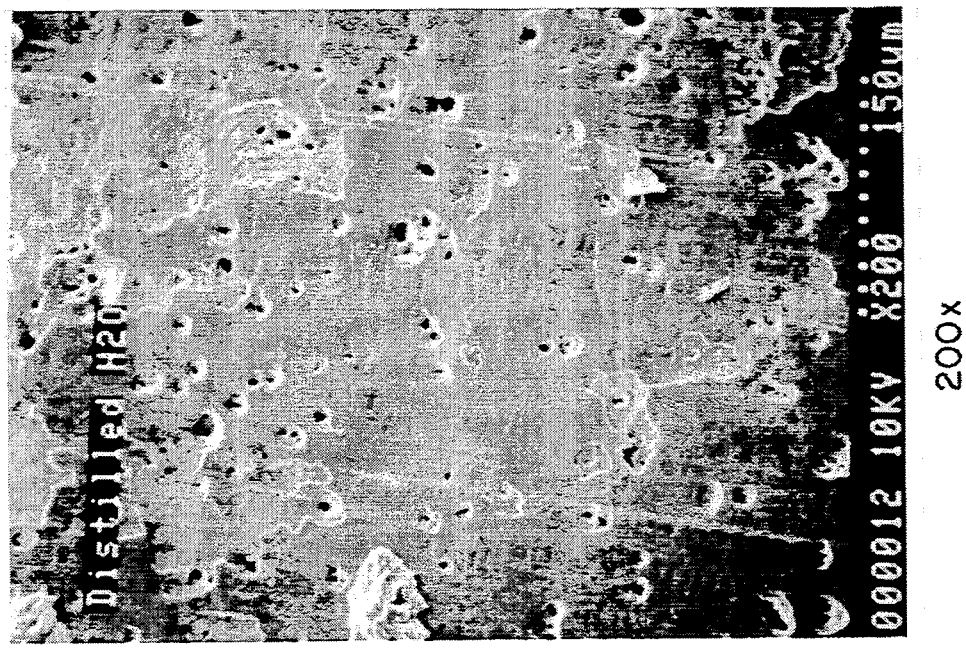
FIG. 5.

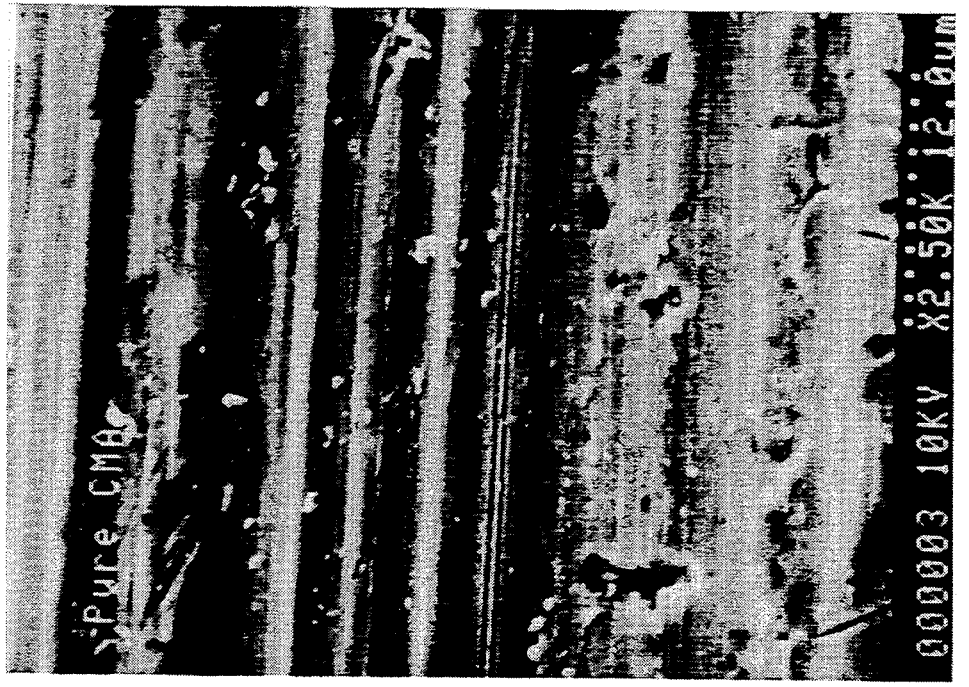
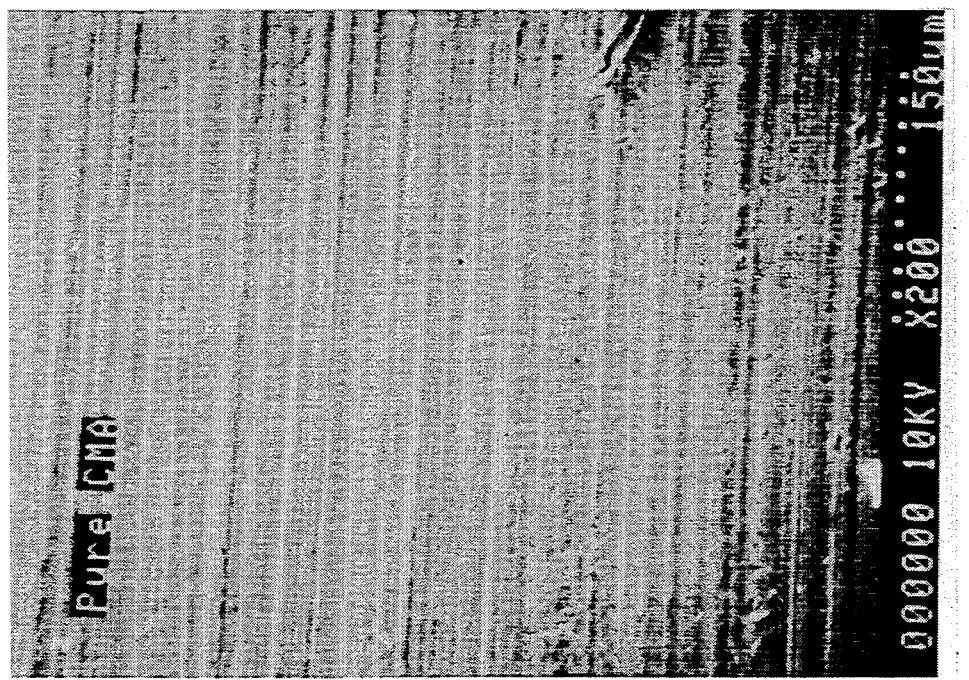
FIG. 6.

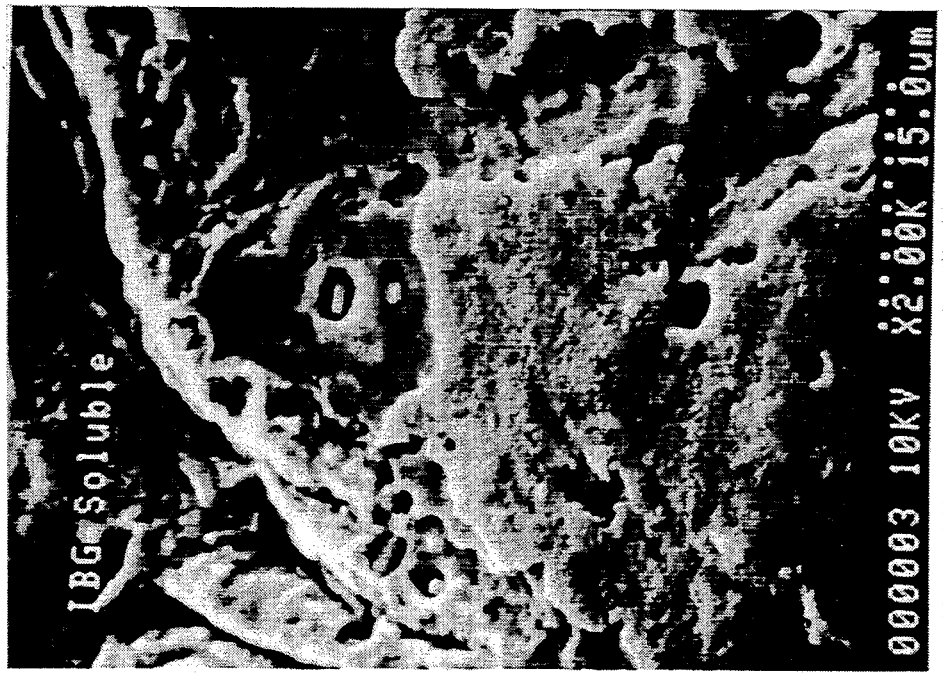
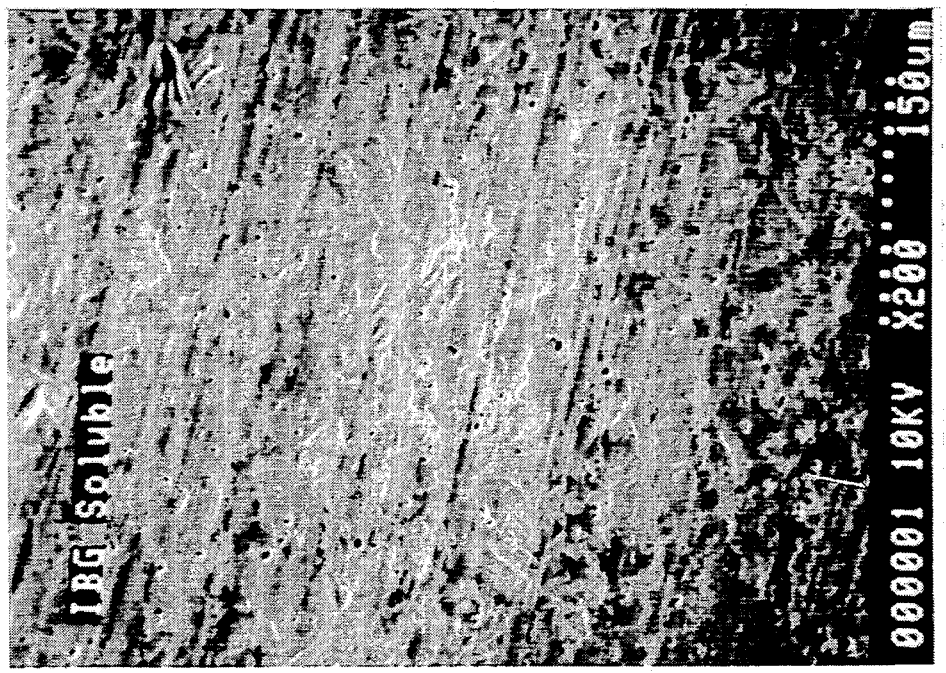
FIG. 7.

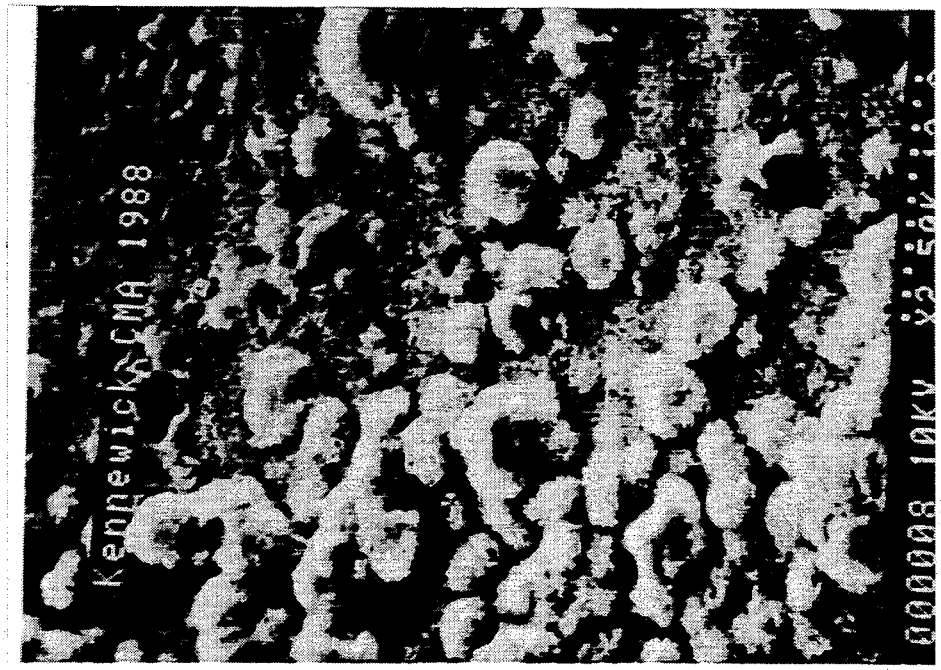
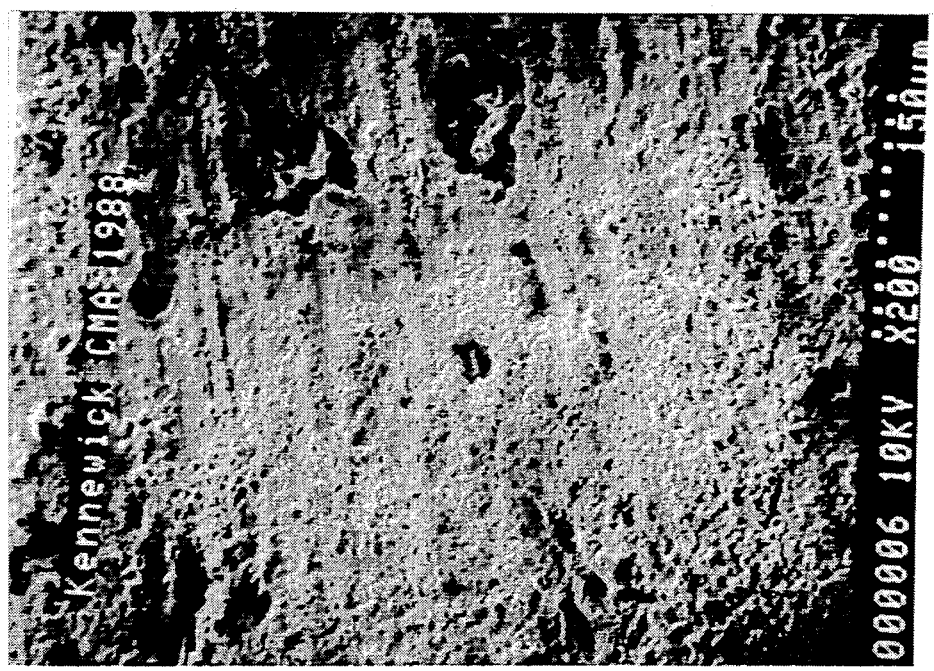
FIG. 8.

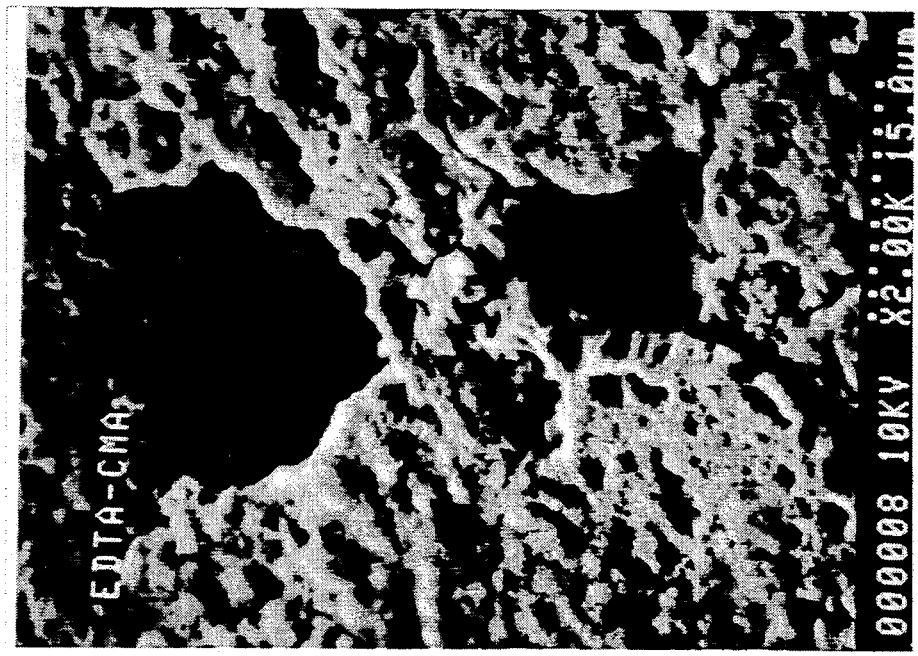
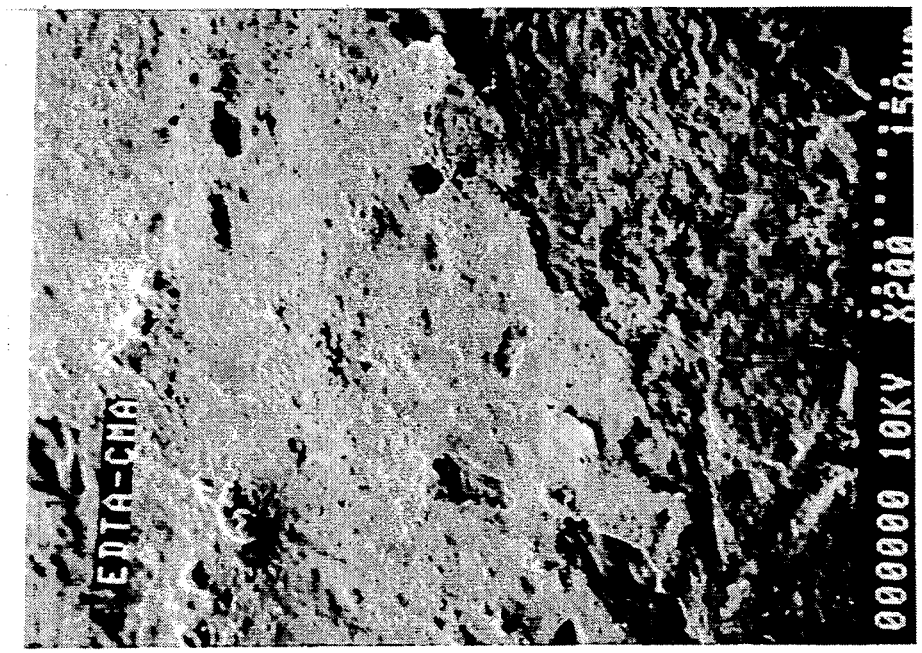
FIG. 9.

EDGE-ON VIEWS OF THE SAMPLE SEEN IN FIG. 9
5000x
(b)
5000x
(a)
FIG. 10.

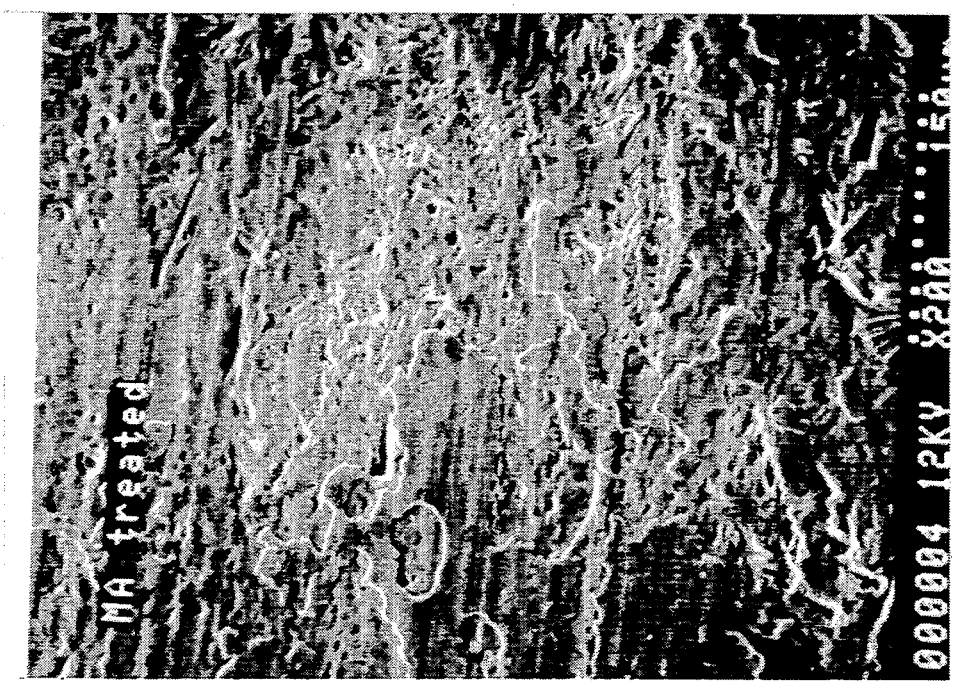
FIG. 11.

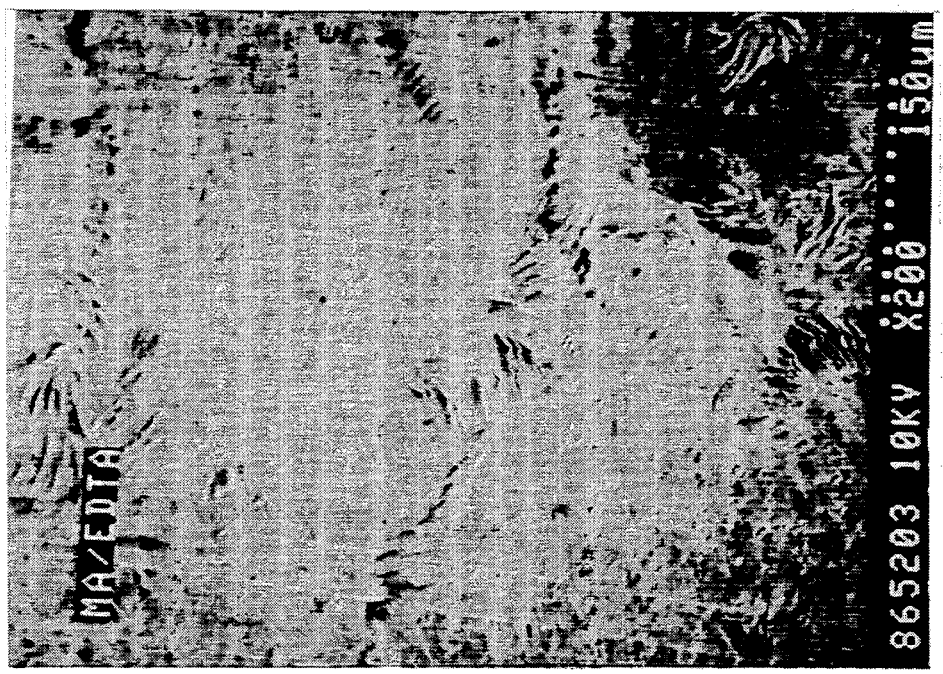
FIG. 12.

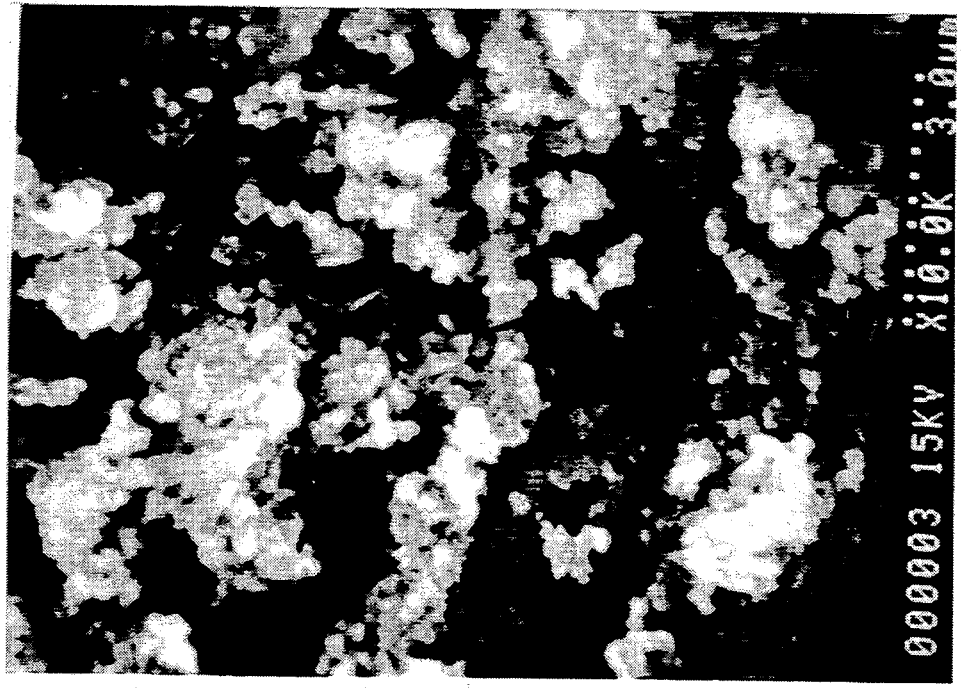
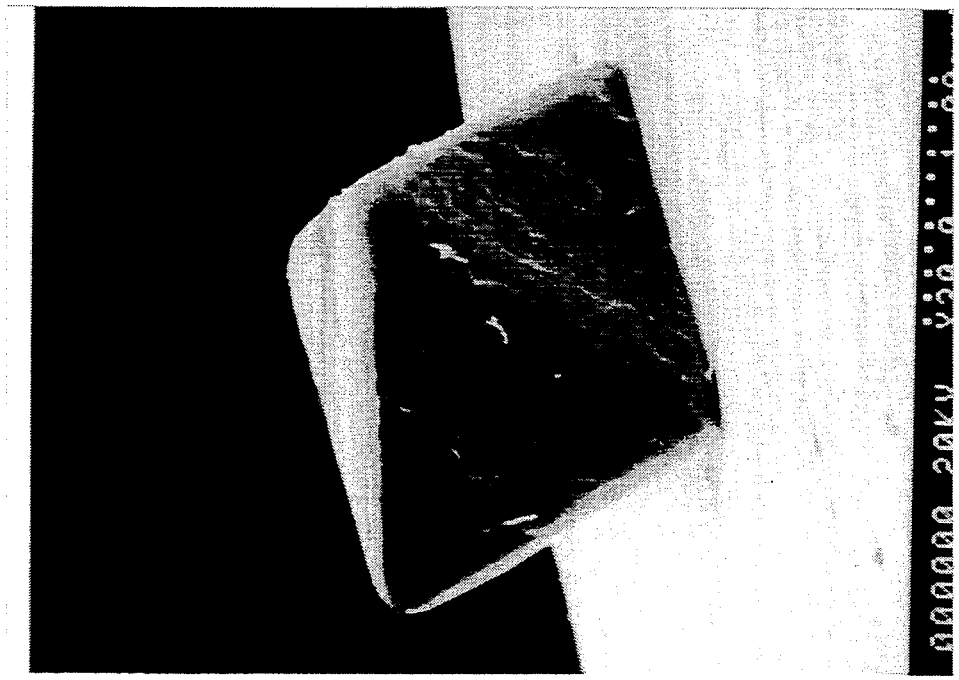
FIG. 14.

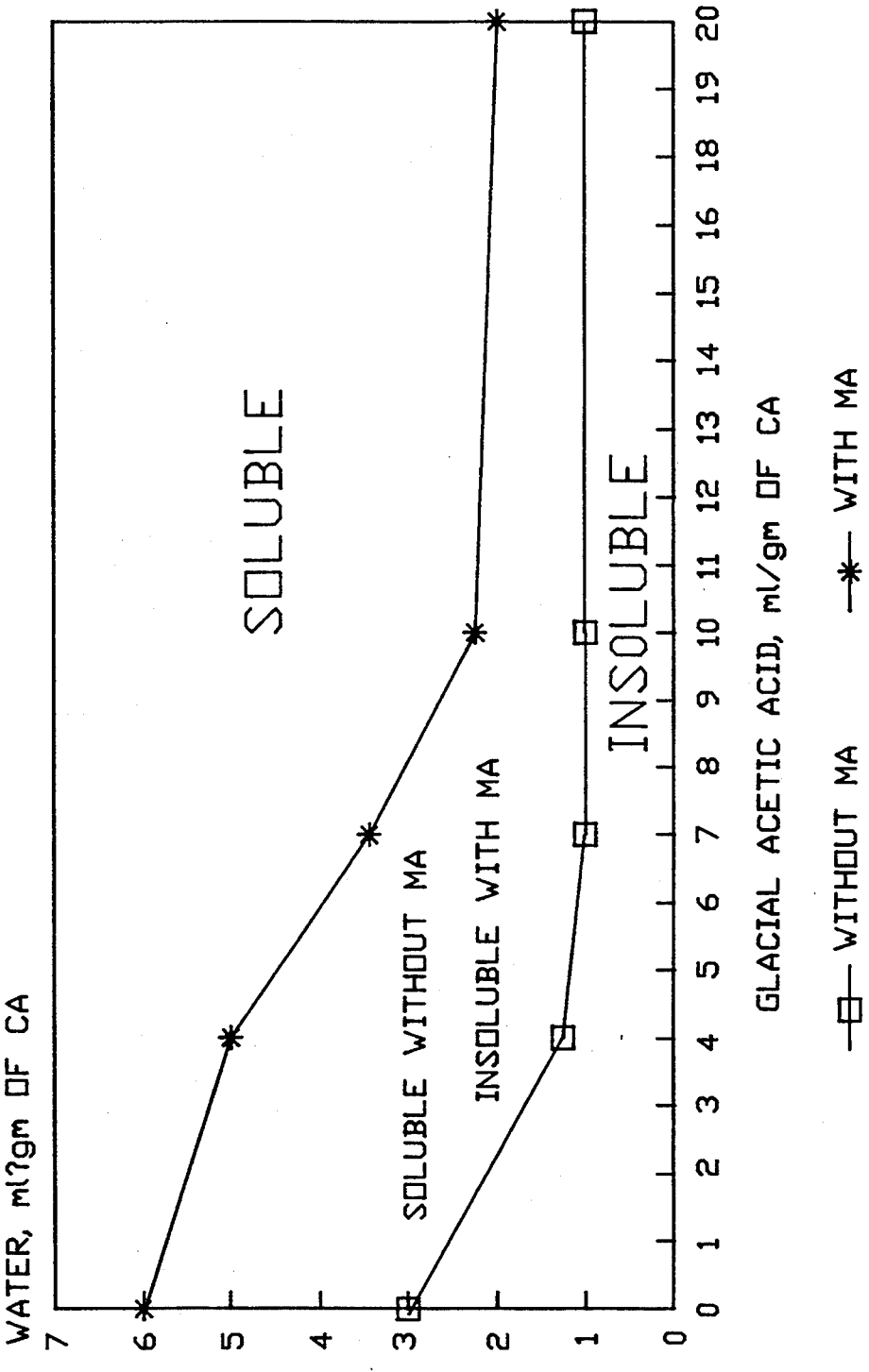

PROCESS FOR MANUFACTURING CRYSTALLINE CALCIUM MAGNESIUM ACETATE

This is a continuation of application Ser. No. 07/431,915, filed Nov. 6, 1989 now abandoned, which is a continuation-in-part of Ser. No. 07/360,369, filed Jun. 2, 1989 now abandoned.

BACKGROUND OF THE INVENTION

Calcium acetate, magnesium acetate and calcium magnesium acetate have recently been the subject of study for use as deicing agents to replace conventional road salt and calcium chloride, both of which have been shown to have undesirable corrosive and environmentally detrimental properties. Among these materials calcium magnesium acetate (CMA) has particularly been the subject of study and efforts have been made to produce it on a commercial scale. See U.S. Pat. Nos. 4,426,308, 4,444,672, 4,511,485 and 4,606,836.

However, a disadvantage to commercially produced CMA has thus far prevented its use as a deicing agent for airport runways and taxiways. It has been found that commercial CMA stains or corrodes the aluminum and aluminum alloys used on aircraft. Unacceptable levels of corrosion to these metals, particularly to aluminum itself, could affect the functioning of the mechanical components as well as the structural integrity of the aircraft.

The currently accepted airport runway deicing compositions are ethylene glycol and urea; however, both have been subject to criticism because of their adverse environmental effects. For example, urea may contaminate lakes and streams and is detrimental to fish and other aquatic life. Therefore, in that the currently acceptable deicing compositions used on airport runways and taxiways are under severe criticism for their environmental disadvantages, and being that other conventional solid deicing compositions used on roads, including previously available CMA, have unacceptable corrosivity for aluminum and aluminum alloys, there is need to develop an alternative deicing composition specifically for use on airport runways and taxiways. To reduce the staining effect of commercial CMA, it has been found to be necessary to use additives (such as chelating compounds).

It is therefore an object of the present invention to provide novel deicing compositions which are useful on airport runways and taxiways.

It is a further object of the present invention to provide a lower cost method of preparing large particles of substantially pure calcium magnesium acetate which do not stain aluminum and do not require anti-staining additives.

These and other objects of the invention will be apparent from the following description and from the practice of the invention.

SUMMARY OF THE INVENTION

A method is provided for preparing large particles of substantially pure crystalline calcium magnesium acetate, which are useful as a non-aluminum-staining deicer. The method comprises forming a homogeneous solution comprising magnesium, acetate, and calcium ions in a solvent comprising an organic liquid in which the solubility of calcium magnesium acetate is less than magnesium acetate or calcium acetate. The solvent may contain water. The temperature of the solution is maintained for a sufficient period of time to form calcium magnesium acetate crystals. Water, if present in the solvent, is removed if necessary, e.g. by evaporation, in order to effect crystallization.

DESCRIPTION OF THE DRAWINGS

FIG. 2 shows the XRD spectra of a commercial magnesium acetate tetrahydrate (2A); a commercial calcium acetate hemihydrate (2B); and crystalline calcium magnesium acetate according to the present invention (2C).

FIG. 4 shows the SEM at 200× and 2000× of a new aluminum pan.

FIG. 5 shows the SEM at 200× and 1000× of an aluminum pan treated with distilled water.

FIG. 6 shows the SEM at 200× and 2500× of an aluminum pan treated with CMA according to the present invention.

FIG. 7 shows the SEM at 200× and 2000× of an aluminum pan treated with CMA made by an aqueous method with gel removed.

FIG. 8 shows the SEM at 200× and 2500× of an aluminum pan treated with CMA made according to an aqueous method.

FIG. 9 shows the SEM at 200× and 2000× of an aluminum pan treated with EDTA-CMA made according to an aqueous method.

FIG. 10 shows two edge-on views (a and b) by SEM at 5000× of the sample depicted in FIG. 9.

FIG. 11 shows the SEM at 200× and 2500× of an aluminum pan treated with magnesium acetate tetrahydrate.

FIG. 12 shows the SEM at 200× and 3000× of an aluminum pan treated with magnesium acetate and sodium EDTA.

FIG. 14 shows the comparative crystal sizes by SEM of commercial CMA particles and crystalline CMA made according to the invention.

FIG. 15 is a graph of the solubilities of CA and CA/-MA(1:2) in solvent mixtures of water and acetic acid at 90° C.

DESCRIPTION OF THE INVENTION

Figure 1:
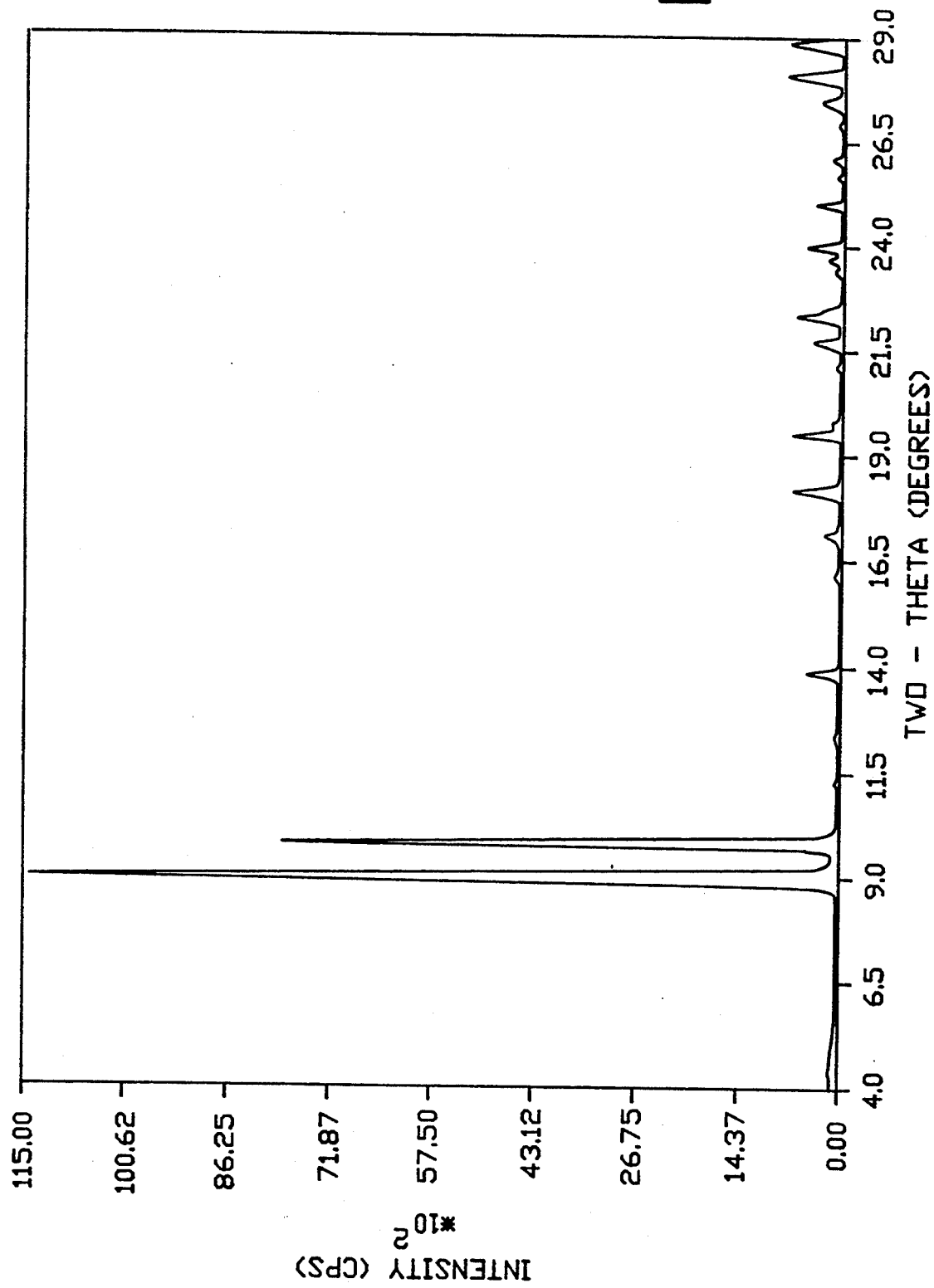
FIG. 1 is an X-ray diffraction (XRD) pattern for crystalline calcium magnesium acetate made according to the present invention.

The present invention is directed to making large particles of substantially pure crystalline calcium magnesium acetate. Since the material is formed as crystals, it can be separated from its mother liquor in substantially pure form which, it is believed, has heretofore not been accomplished for large scale preparation of CMA. The crystal size from the present process is generally larger than 0.1 mm, and many times larger than several millimeters. Compared with the particles or crystals in commercially available CMA, which are usually smaller than 1 μm, the crystals made in accordance with the present invention are several orders of magnitude larger. A commercial method of making CMA involves formation of the CMA in an aqueous environment in which all of the reactants are soluble and in equilibrium with the CMA product, thus resulting in a CMA-containing solid which is contaminated, in various amounts, with calcium acetate, magnesium acetate, and/or unreacted magnesium oxide or hydroxide, and trace metals (Fe, Al, Si, etc.). The pertinent reactions in an aqueous solution are as follows:

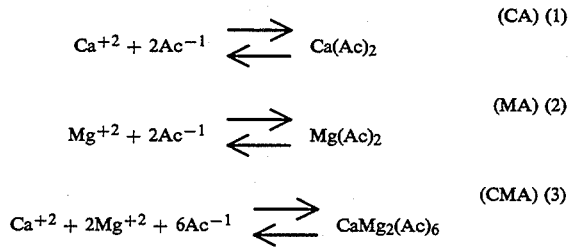

The existence of these equilibria may be shown by dissolving CMA crystals in water, allowing it to equilibrate, and isolating the products. Calcium acetate (CA) and magnesium acetate (MA) are found in greater amounts than indicated by the purity of the original CMA crystals.

According to the present invention, the crystalline CMA obtained, once separated from the mother liquor, is substantially pure. As used herein, the term "substantially pure" means 0.5% by weight or less of impurities, as determined by both X-ray diffraction (XRD) and TGA-GC-MSD analysis. Analysis by XRD alone or elemental analysis is not sufficient to determine purity of CMA since the amounts of amorphous phase MA and MgO are not determined by XRD. TGA (trace gas analysis) quantitatively measures weight loss from a sample as a function of rising temperature.

For example, since CMA is anhydrous, any weight loss below 200° C. is due to the dehydration of CA and MA. If a significant weight loss is seen below 200° C., the tested CMA is not pure. However, this weight loss alone cannot be used to quantitatively determine the amount of CA and MA in the sample. Starting at 300° C., MA decomposes, $MgCO_3$ is formed, and acetone is evolved. $MgCO_3$ then quickly decomposes at a slightly higher temperature (340° C.). CMA starts decomposing at 350° C. Its peak of acetone evolution is around 380°–390° C. CA decomposes above 400° C. The following reactions describe the decomposition mechanism:

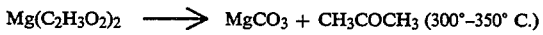

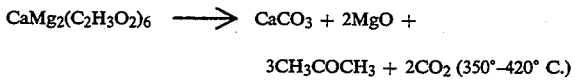

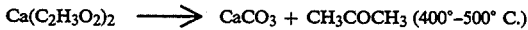

The CMA decomposes and produces acetone and carbon dioxide at the same time. However, CA decomposes and evolves only acetone. By comparing the acetone and carbon dioxide evolution, one can resolve CA and CMA from their partially overlapped acetone evolutions.

The resolution of MA and CMA from the acetone evolution curve may be accomplished because their decomposition temperatures are about 50° C. apart. By selecting a breaking temperature around 350° C. where the valley of the acetone evolution curve is located, an integration of the acetone evolution curve under the three regions can be used to determine relative mole ratios of CA, MA, and CMA from their partially overlapped acetone evolutions.

The substantially pure CMA produced according to the present invention is non-staining on aluminum surfaces, which is advantageous for use as a deicing agent in airports on taxiways and runways.

Commercially produced bulk CMA contains impurities which cause aluminum staining. While not intending to be bound by any particular theory, it is believed that a major source of the staining is magnesium oxide or hydroxide present from unreacted starting materials or from decomposition of product CMA. It is also believed that, due to its purity and large crystal size, the CMA according to this invention has improved deicing capacity over small crystal-sized CMA made in aqueous media.

To prepare the substantially pure CMA according to a preferred embodiment of the present invention, the magnesium, calcium and acetate ions must be provided in a solvent in which the solubility of CMA is less than the solubility of either CA or MA for crystallization to take place. Preferably, magnesium acetate may be dissolved in such a solvent, preferably glacial acetic acid, usually accompanied by heating. A preferred solvent is glacial acetic acid, which, by heating to about 40° C. the magnesium acetate (usually presented as $Mg(Ac)_2 \cdot 4H_2O$), provides a clear solution. Heating up to a temperature in the range of about 40° C.–60° C. will be sufficient.

The calcium acetate (usually provided as its hydrate $Ca(Ac)_2 \cdot \frac{1}{2}H_2O$) may be similarly dissolved in the same or a different solvent. The calcium acetate should normally be heated to above about 90° C. if a non-aqueous or substantially nonaqueous solvent is used. Heating up to a temperature in the range of about 90°–120° C. will be sufficient.

To assist in this dissolution of the calcium acetate, magnesium acetate, magnesium oxide, dolomite or other source of magnesium, calcium and/or acetate ions, it may be convenient to add water to the solvent. However, if too much water is in the solvent, CMA may not crystallize without further modification of the solvent. Thus, once the initial solids are dissolved, the water in the solvent will usually be removed. After sufficient reduction of the water content of the solvent, the CMA will crystallize. The preferred method of removing water is by evaporation but other methods of removing water may be used, such as by molecular sieving, adding dehydrating agents (such as acetic anhydride), etc.

Preferably, but not necessarily, two separate solutions respectively containing calcium acetate, or other calcium source, such as dolomite, CaO, or lime, and magnesium acetate, or other magnesium source, such as dolomite or MgO, will first be formed, then the two solutions will be combined. In such an instance, if the two solvents are different, they should be selected so as to be miscible. Alternatively, both the calcium acetate and magnesium acetate, preferably as their hydrates, may be dissolved together in the same solution. If the solvent is non-aqueous or substantially non-aqueous, it should be heated at least to about 90° C. in order to dissolve the CA.

Alternatively, CaO (lime) may be used as the calcium ion source. To dissolve lime, some water may initially be needed in the solvent. Upon mixing with dissolved magnesium ions (preferably, in acetic acid), crystallization of CMA will commence after a sufficient amount of the water in the solvent has been removed.

Similarly, MgO, which is readily soluble in glacial acetic acid, may be used as the source of magnesium ions.

Once the dissolved calcium, acetate and magnesium ions are mixed, the CMA will crystallize typically by allowing the solution to stand, at a high temperature. If the solvent is substantially organic, e.g. acetic acid, the temperature should be maintained above about 60° C., and preferably in the range of about 80° to 120° C., while the CMA crystals are formed. If the solvent contains too much water, for CMA to crystallize, then some water should be removed therefrom, usually by heating from about 40° C. to about 120° C., until the water content of the solvent is sufficiently low to allow CMA crystals to form. Depending on the concentration of the respective components in the solution, crystallization could take up to several days.

According to another embodiment of the invention, the CMA may be made by rapid crystallization of the solutions of CA and MA. The crystal size of rapidly made CMA is generally smaller than 0.1 mm. Some CA and MA may be trapped in the CMA crystal structure in the rapid nucleation process. Such CMA crystals, although, less pure, are free of mineral and raw material impurities (e.g. MgO), and thus may be commercially useful as a non-aluminum staining deicer.

Referring to FIG. 15 there is shown a graph of the solubility at 90° C. of calcium acetate hemihydrate as a function of the relative amounts of water and acetic acid in a water-acetic acid solvent. In the lower curve, wherein only calcium acetate hemihydrate is present in the solvent, it can be seen that once there is over about 7 mls of acetic acid per gram of calcium acetate used in this solvent, then only about 1 ml of water per gram of calcium acetate need be present in the solvent to dissolve the calcium acetate. In the upper curve, calcium acetate hemihydrate is present in the solvent in a 1:2 mole ratio with magnesium acetate tetrahydrate. Under these conditions it can be seen that once there is over about 10 mls of acetic acid in the solvent per gram of calcium acetate, it only requires about 2 mls of water per gram of calcium acetate in the solvent present to dissolve the calcium acetate. This in general shows that when large amounts of acetic acid are used with respect to calcium acetate, then only 1 ml of water per gram of calcium acetate or, in the presence of magnesium acetate, 2 mls of water per gram of calcium acetate, are required in the solvent to dissolve the calcium acetate. The dissolution of magnesium acetate is usually no problem because of its solubility in glacial acetic acid is greater than calcium acetate.

The amount of calcium relative to magnesium is not particularly critical. The crystalline product formed has the empirical formula $CaMg_2(Ac)_6$. The excess, if any, of magnesium ions, calcium ions and acetate ions remain in the solution. Thus the substantially pure CMA may be physically separated from the mother liquor.

While not intending to be bound by any particular theory, it is believed that by performing the process in a non-aqueous solution, there is essentially a molecular reaction wherein the reactants are molecular calcium acetate and magnesium acetate in a non-aqueous solvent cage, rather than the ionic species present in an aqueous solution. Therefore, in a non-aqueous environment the equilibria shown in equations [1], [2] and [3] above do not exist and the reaction to form CMA crystals is irreversible. Since CMA is soluble in water at room temperature (solubility is about 29%, i.e., 10 grams of CMA in 24 grams of water), to maximize the yield of crystalline CMA, it is desirable to minimize the water content in the mother liquor. However, crystalline CMA can be obtained from a crystallizing solvent containing a large amount of water, but the yield declines at a ratio of about 10 grams of CMA per each additional 24 grams of water. Usually, therefore, there should be less than about 20%, and preferably less than about 10% by weight of water in the crystallizing solvent. A large amount of water may therefore be used initially to dissolve the CA, MA, dolomite, MgO, or other source of calcium and/or magnesium ions, then, to effect crystallization of CMA, the water may be removed. When the water content of the solvent is sufficiently low, the CMA crystals will form. Therefore, initially, solvents containing 50% by volume or more of water may be used to dissolve the starting materials.

As a further advantageous feature of the present invention, it is believed that aluminum staining may be promoted by alkaline environments. The crystalline CMA made according to the present invention, when redissolved in water, has a pH of less than 8, usually about 7.2, indicating substantial neutrality, which is believed to augment its non-staining properties. Furthermore, the crystalline CMA contains less than 0.5% of impurities, indicating substantial purity.

The CMA crystals may be separated from the non-aqueous mother liquor by conventional purification procedures, such as by filtration or precipitation, and the like. The excess acetic acid may be removed either by an evaporation or solvent-washing technique.

The CMA made according to the present invention may be used in a deicing composition in its crystalline form. The CMA according to the present invention may also be optionally mixed with a traction aid, which is a material which improves traction when applied to a slippery surface, including, but not limited to, inert supports such as sand, pulverized corncobs, nutshells (such as walnut shells, pecan shells, and almond shells), expanded shale, vermiculite, pumice, cinders or other substantially insoluble materials with good anti-slip properties. Additives may be also used with the CMA, such as sodium chloride, EDTA, glycols, etc., if desired, although some of such additives may detract from the anti-corrosive and anti-staining properties of the CMA crystals.

Having described the preferred embodiments of the invention, the following examples are presented for purposes of illustration and are not intended to limit the invention in any way.

EXAMPLE 1

CMA from MA and CA

Five grams of magnesium acetate tetrahydrate was dissolved in 100 ml glacial acetic acid by heating to 40° C. One gram of calcium acetate hemihydrate was dissolved at 110° C. in 50 ml glacial acetic acid, then diluted with 50 ml of boiling glacial acetic acid. The calcium acetate solution was added slowly to a flask containing the magnesium acetate, which was maintained at about 110° C. After all of the calcium acetate solution was added (over a period of several hours; no precipitate was formed), the mixture was maintained at a temperature of at least 80° C. overnight, by which time crystalline calcium magnesium acetate was formed.

EXAMPLE 2

CMA from MA and CA

Fifteen grams of magnesium acetate tetrahydrate in glacial acetic acid (600 ml) was dissolved by heating at about 40° C. Three grams of calcium acetate hemihydrate was dissolved in glacial acetic acid (500 mls) at 110° C. The two solutions were immediately combined and maintained at 88° C. for 7 days. Crystalline calcium magnesium acetate was formed.

EXAMPLE 3

CMA from CA and MA

Five grams of magnesium acetate tetrahydrate was dissolved at 40° C. in 150 mls glacial acetic acid. One gram of calcium acetate hemihydrate was dissolved in 100 mls of glacial acetic acid at 110° C. The solutions were immediately combined and maintained at 77° C. for about two days. The calcium magnesium acetate crystals formed were larger than those crystals formed in Examples 1 and 2. The crystals were washed with glacial acetic acid to remove the excess CA and MA. The crystals were then dried in a vacuum oven. The CMA crystals have a distinct morphology. The X-ray diffraction pattern of the CMA made in accordance with Example 1 is shown in FIG. 1.

Figure 3B:
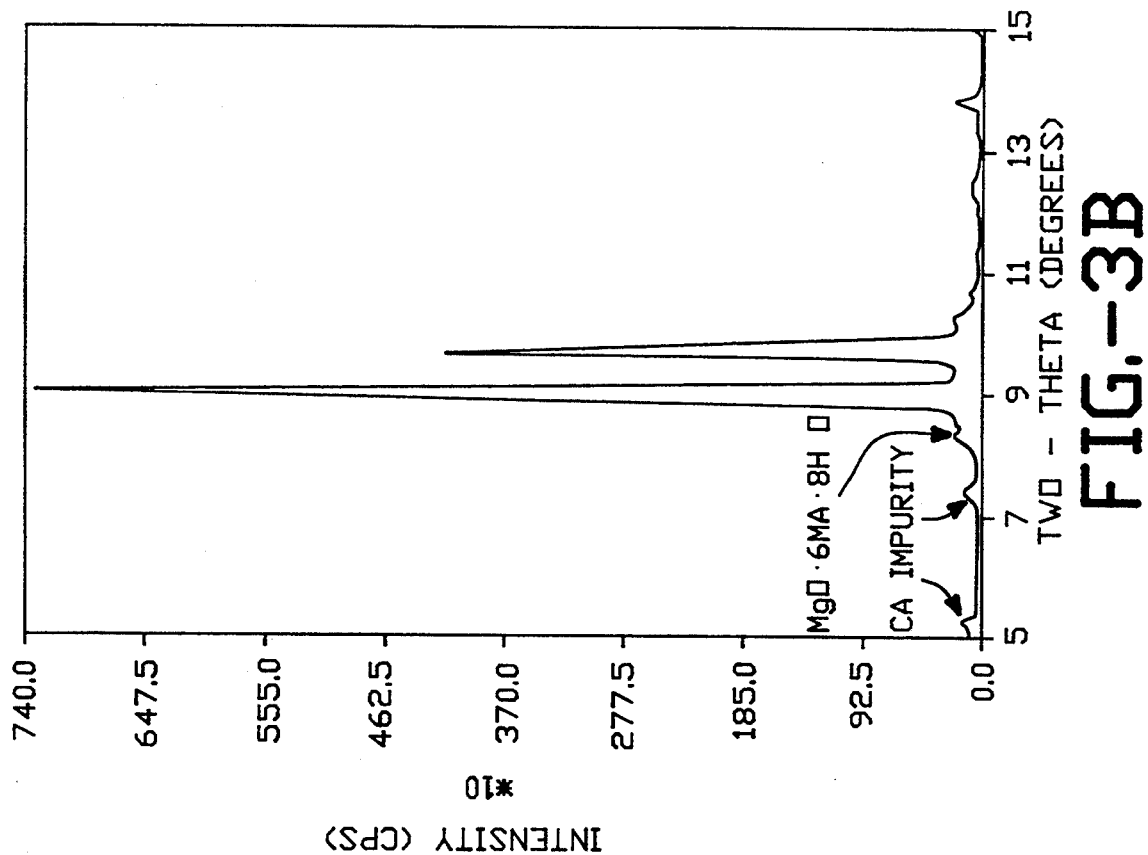
FIG. 3A & B shows the XRD spectra of CMA made according to the present invention (FIG. 3A) and CMA made according to an aqueous method (FIG. 3B).
Figure 3A:
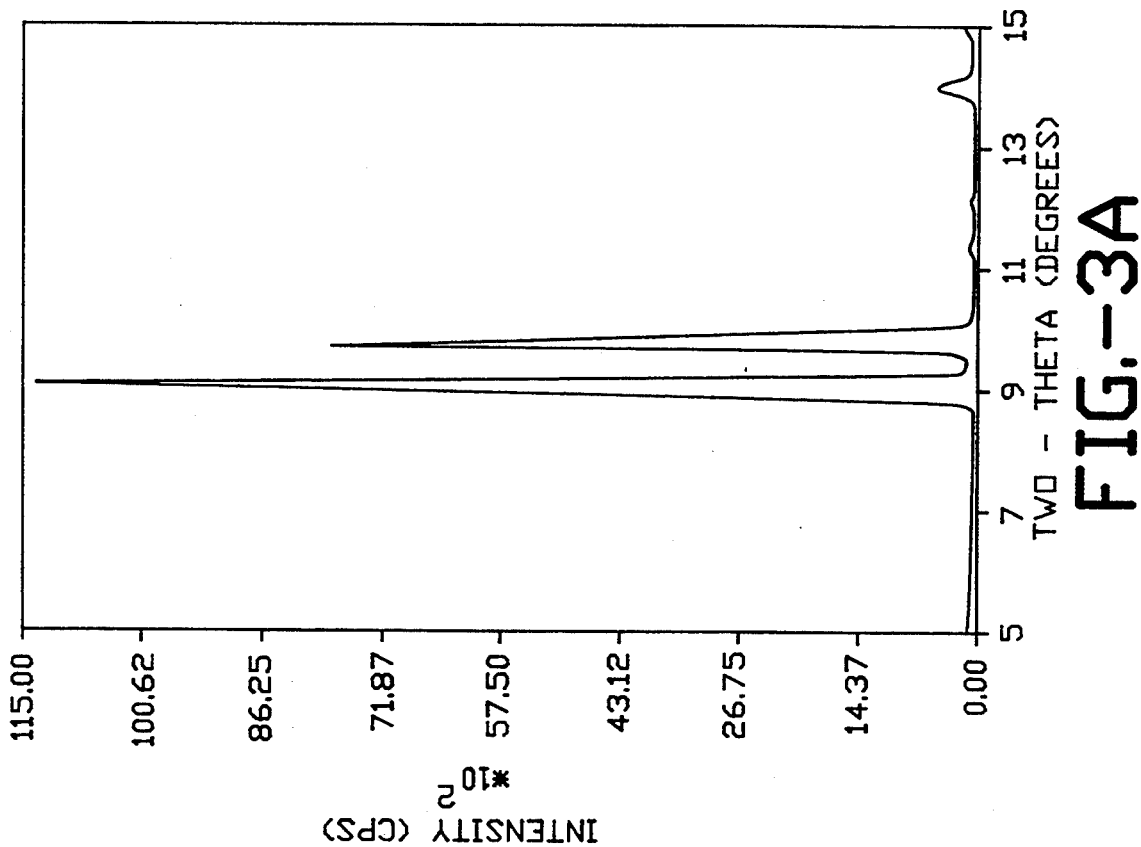

Referring to FIG. 2, there is shown an X-ray diffraction (XRD) pattern of amorphous magnesium acetate tetrahydrate (MA) (FIG. 2A), calcium acetate hemihydrate (CA) (FIG. 2B) and the calcium magnesium acetate crystalline material according to the present invention (CMA) (FIG. 2C). FIG. 3 shows the XRD pattern of crystalline CMA according to the present invention (FIG. 3A) and a sample of CMA made by aqueous methods (FIG. 3B) by reacting calcium oxide and magnesium oxide with acetic acid. As can be seen in FIG. 3B, there is a shoulder (outlined by the dotted line) between about 7 and 10 degrees 2Θ which indicates the presence of magnesium acetate. The peaks at about 5 and 7 degrees 2Θ also indicate the presence of calcium acetate. The heights of these peaks relative to the two large CMA peaks is descriptive, i.e., based on quantitative XRD patterns of the two pure phases of the CA content of the material in FIG. 3B in the 10 to 15 weight percent range. Referring to FIG. 14, there is shown (FIG. 14A) a single CMA crystal made according to the invention, magnified 30 times. FIG. 14B shows CMA particles made by an aqueous method, magnified 10,000 times.

EXAMPLE 3A

Fifty grams of calcium acetate hemihydrate and 130 grams of magnesium acetate were dissolved in 500 ml of acetic acid and 150 ml of water at 90° C. in a 1000 ml beaker. The beaker was covered with a watchglass (not airtight) and maintained at 90° C. for two days, after which the volume had been significantly decreased by evaporation of both water and acetic acid. The CMA crystals had formed during this period.

EXAMPLE 3B

Another sample was prepared and treated exactly as described in Example 3A except that the beaker was sealed to prevent solvent evaporation. No CMA solids formed.

EXAMPLE 4

CMA from lime and MA

A sample of 0.5 g CaO was added to 50 ml glacial acetic acid and 50 ml H$_2$O solution. The solution was heated to >80° C. The cloudy solution turned clear. Then 2 g of MA was added to 100 ml glacial acetic acid. The two solutions were mixed. About a day later, after most of the water had evaporated from the solution, CMA crystals were formed.

EXAMPLE 5

CMA from CaO and MgO

About 100 g CaO was added to 2000 ml glacial acetic acid and heated to boiling. Then 150 ml H$_2$O was added, followed by addition of about 900 ml of H$_2$O. About 237 g MgO was mixed with 2000 ml glacial acetic acid, 550 ml H$_2$O was then added and the solution was heated under stirring for overnight. A very thick solution (transparent) was formed. The above two solutions were mixed and split into two beakers. More water ($\approx$2000 ml) was added to these two beakers. After heating for several days, pure CMA crystals were collected.

EXAMPLE 6

CMA from Dolomite and Reagent Grade MgO

About 10 g of dolomite was mixed with 1000 ml glacial acetic acid, then heated to boiling. After adding 40 ml of water to the boiling solution, it immediately turned from a milky color to transparent.

About 20 g of reagent grade MgO (Allied Chemical) was mixed with 1000 ml glacial acetic acid. The solution was totally clear after 2 hours stirring and heating.

The two solutions were mixed at about 100° C. Another 60 ml of H$_2$O was added to clear the cloudy solution.

After heating for about 1 day, white crystals were formed.

TGA-GC-MS indicated that the crystals were very pure.

EXAMPLE 7

CMA from Dolomite and MgO

About 21 g MgO (National Magnesia Chemicals) was added into 1000 ml glacial acetic acid and 50 ml of H$_2$O was added to enhance the dissolution. The solution was heated to 70° C. Unlike the reagent grade MgO, the solution was red-brownish.

About 10 g of dolomite was added into 1000 ml of glacial acetic acid. The solution turned a milky color even at boiling. However, after adding 40 ml to the solution, the solution cleared.

The two above-described solutions were mixed and another 50 ml of water was added. The solution was then kept at 100° C. for several days. After most of the water had evaporated, the total solution volume dropped down to less than 1000 ml and CMA began to crystallize.

EXAMPLE 8

Al corrosion tests

The following solutions were used to test aluminum corrosion:

| No. | Solution | pH | Test Results |
| --- | --- | --- | --- |
| 1 | None | N/A | Control 1 |
| 2 | Distilled Water (DW) | N/A | Control 2 |
| 3 | 250 mg CMA crystals/ 10 ml DW | 7.2 | Pass |
| 4 | 500 mg 1988 Kennewick CMA/ 20 ml DW; Gel Removed | 9.8 | Pass |
| 5 | 250 mg 1988 Kennewick CMA/ 10 ml DW | 9.8 | Fail |
| 6 | 250 mg 1988 Pilot Plant EDTA-CMA/10 ml DW | 9.9 | Fail |
| 7 | 250 mg MA/10 ml DW | 8.0 | Fail |
| 8 | 250 mg MA/200 mg Na-EDTA/ 10 ml DW | 5.5 | Fail |
| 9 | 250 mg CMA crystals/ 50 mg MgO/10 ml DW | 9.7 | Fail |

Four Al pans were soaked in each of the solutions for at least 1 week. There was no intentional agitation during the soaking period. The samples for SEM (scanning electron microscope) analysis were prepared by ultrasonicating the Al pan in de-ionized water for about 5 minutes, drying it with an air nozzle and then coating it with 3–5 nm of Pd-Au.

The pH values of the above solutions were measured with a Cole-Parmer Model 5985-80 digital pH meter, which was calibrated with two buffer solutions with pH 7 and 10. The pH value for a regular distilled water ranges from 5.8 to 8 depending strongly on trace amounts of impurities in it.

1. The images (at 200× and 2000× magnification) of the new Al pan (FIG. 4) served as references for comparison. The natural oxide film was so thin that there was no detectable oxygen peak in the EDX (Energy Dispersive X-Ray) analysis.
2. The surface of the distilled water sample (sample 2) showed many large pits. It was covered to a large extent by a layer of aluminum oxygen compounds (FIG. 5). This layer is responsible for the darker color appearance. There are also isolated clusters of large crystals. These crystals were verified by EDX analysis to contain only Al and O (H is not detectable by EDX analysis).
3. The Al pan soaked for 2 weeks in the solution made from pure CMA crystals made according to the invention (solution 3) showed practically no sign of corrosion (FIG. 6). There were a few isolated aluminum-oxygen crystals about 1 micron in size. Its surface was practically indistinguishable from the new Al pan.
4. The gel-free solution was prepared by dissolving 500 mg of the commercial CMA pellets made by an aqueous method at Kennewick, Wash., in 20 ml of water. The solution was then allowed to sit for a day after ultrasonication. An eyedropper was used to take out about 3 ml of solution from the top of the vial without disturbing the gel at the bottom. Al pans were then placed in the clear solution (solution 4).

After 10 days, a discontinuous aluminum-oxygen film was observed on the surface. This film, in places, was several layers thick (FIG. 7). The surface not covered by this film appeared to be etched. It showed holes similar to the surface of the sample treated in distilled water, although the holes were much smaller. Often there were small particles situated inside these holes. These particles contained Fe and Mg.

5. The sample soaked in the CMA made at Kennewick without removal of the gel (solution 5) showed the usual thick manasseite film with its characteristic lumpy appearance (FIG. 8). No Si was detected in this film by EDX analysis. Almost the entire surface was covered by this manasseite film.
6. The EDTA-CMA (CMA made by an aqueous method and containing EDTA (solution 6, made at Richmond, Calif.) treated Al pan showed two circular rings of reaction product. It is not clear why this is so although it was possibly due to the way the pan was sitting on the bottom of the vial. The reaction product was manasseite. In many places the film appeared to be not well anchored to the bulk of the Al pan (FIG. 9). An oxide film was clearly present in the areas that were not covered by the film. Cracks can be seen in this oxide film, but its thickness has not been determined. Close examination of the images suggested that the film was a mixture of aluminum-oxygen block particles and manasseite crystals.

The images taken at high tilt angles (FIGS. 10(a) and (b)) provided edge-on views of the film. They showed that the manasseite film was formed on the top of a much thicker aluminum-oxygen film. This oxide film was partially detached from the bulk.

Figure 13:
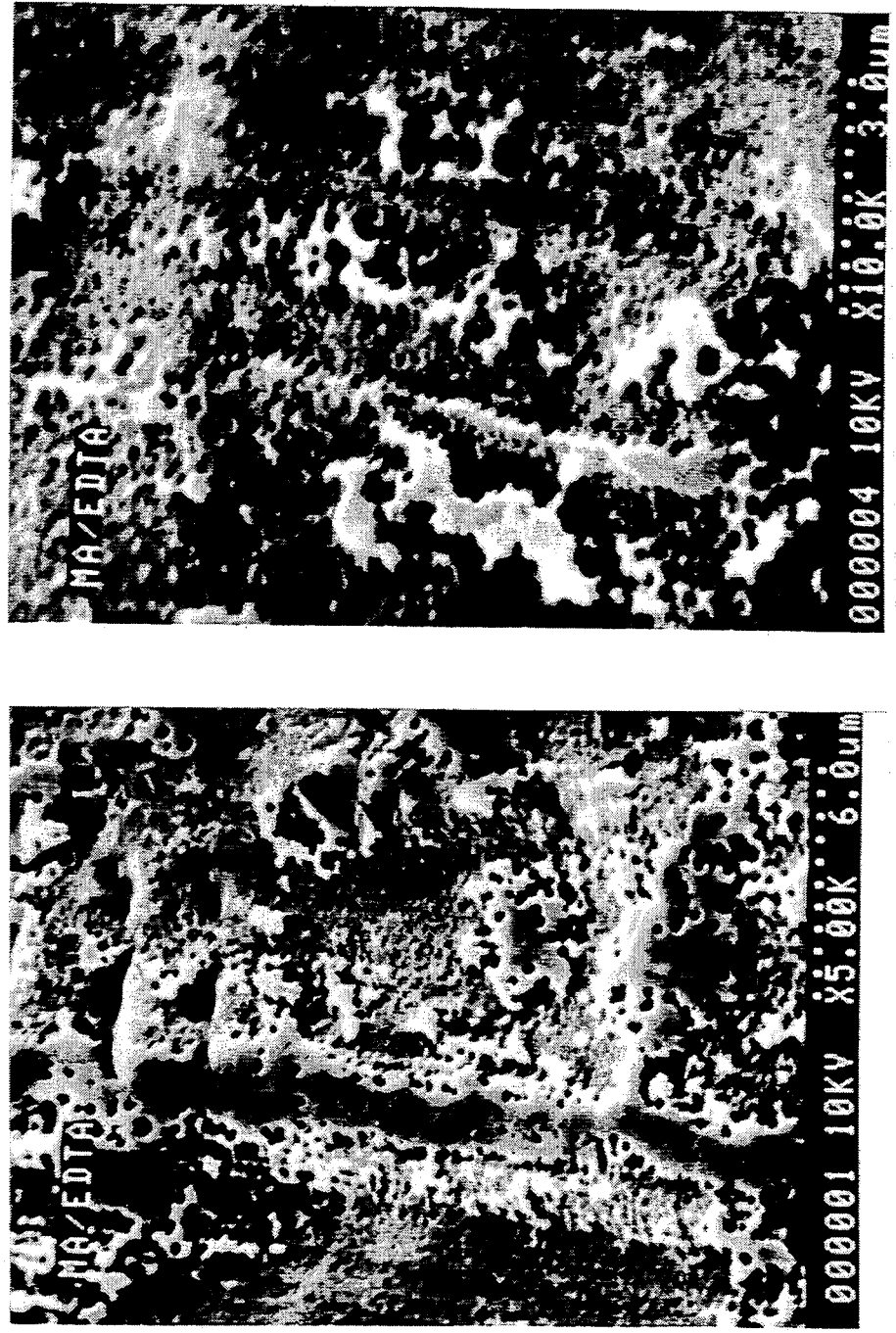
FIG. 13 shows the SEM at 5000× and 10,000× of the sample shown in FIG. 12.

7. The Al pan treated with the MA solution (solution 7) contained a thin film of reaction product. The coverage was small (FIG. 11). Nonetheless at high magnification this film resembled manasseite but the crystals were much smaller than those seen on the samples treated with the Kennewick IBG solution and the EDTA-CMA solution. There were lumps on the surface of the film. However, EDX analysis showed only a small Mg peak. This suggests that the film was mostly aluminum-oxygen compound and very little manasseite. The rest of the exposed areas appeared to be etched when seen in low magnification. These areas were covered with a thin film of aluminum-oxygen compound. This film is thin because substantial subsurface charging can be seen in the images.
8. The surface of the pan treated with the MA-EDTA (Na salt) solution (solution 8) also appeared etched, similar to the sample treated with MA only. No surface film was found but there were patches of particles (FIG. 12). At high magnification (FIG. 13), these patches looked like an overlaid layer containing small holes. The background surface showed a finely pitted texture. It is not clear what that overlaid layer was. In the EDX spectra, there may be a trace of O but not detectable Mg. It may be a very thin layer of alumina or it could be related to the EDTA.
9. Although there was no detectable manasseite and aluminum oxide formed in a pure CMA solution made according to the invention, a significant amount of manasseite was observed when MgO was added to the solution (solution 9). The corrosion result after one week of soaking is comparable to that treated by the CMA of solution 5.

Having described the preferred embodiments of the present invention, it will be apparent to those of ordinary skill in the art that various modifications and alterations are readily apparent without departing from the scope and spirit of the invention. These modifications and alterations are intended to be within the scope of the invention and the invention is not to be limited except by the following claims.

It is claimed:

1. A method of making crystalline calcium magnesium acetate comprising the steps of:

(a) forming a first solution comprising magnesium and acetate ions, in a first substantially non-aqueous solvent;
(b) forming a second solution comprising calcium and acetate ions, in said first non-aqueous solvent or a second substantially non-aqueous solvent;
(c) combining said first and second solutions and maintaining the resultant mixture at a sufficient temperature for a sufficient period of time to form said crystalline calcium magnesium acetate.

2. A method of making crystalline calcium magnesium acetate comprising the steps of:
(a) forming a solution comprising calcium, magnesium and acetate ions, in a substantially nonaqueous solvent; and
(b) maintaining said solution at a sufficient temperature for a sufficient period of time to form said crystalline calcium magnesium acetate.

3. A method according to claim 1 or 2 wherein said temperature for crystallizing said calcium magnesium acetate is in the range of about 80° to 120° C.

4. A method according to claim 1 wherein said step (a) comprises heating magnesium acetate, or a hydrate thereof, in said first solvent to a temperature of at least about 40° C.

5. A method according to claim 1 wherein said step (b) comprises heating calcium acetate, or hydrate thereof, in said first or second solvent to a temperature of at least 80° C.

6. A method according to claim 1 wherein said first and second non-aqueous solvents comprise glacial acetic acid.

7. A method according to claim 2 wherein said step (a) comprises heating calcium acetate, magnesium acetate, or hydrates thereof, in said solvent to a temperature of at least 80° C.

8. A method according to claim 2 wherein said non-aqueous solvent comprises glacial acetic acid.

9. A method according to claim 1 or 2 wherein at least a portion of said calcium ions are provided by dissolving lime.

10. A method according to claim 1 or 2 wherein at least a portion of said magnesium ions are provided by dissolving magnesium oxide.

11. A method according to claim 1 or 2 wherein at least a portion of said calcium ions are provided by dissolving dolomite.

12. A method according to claim 1 or 2 wherein at least a portion of said magnesium ions are provided by dissolving dolomite.

13. A method according to claim 1 or 2 wherein said crystalline calcium magnesium acetate has the formula $CaMg_2(C_2H_3O_2)_6$.

14. A method of making crystalline calcium magnesium acetate comprising the step of rapidly nucleating a substantially non-aqueous solution of magnesium, calcium and acetate ions to form crystalline calcium magnesium acetate substantially free of mineral and raw material impurities.

15. Crystalline calcium magnesium acetate made by the process of claim 14.

16. A method according to claim 1 wherein said first or second substantially non-aqueous solvents comprise less than about 20% by weight of water.

17. A method according to claim 2 wherein said substantially non-aqueous solvent comprises less than about 20% by weight of water.

18. A method of preparing calcium magnesium acetate solids comprising the steps of
(a) forming a solution comprising calcium, magnesium and acetate ions in a homogeneous solvent comprising an organic liquid and, optionally, water; wherein the solubility of calcium magnesium acetate in said organic liquid is less than the solubility of either calcium acetate or magnesium acetate in said organic liquid;
(b) forming solids comprising calcium magnesium acetate from said solution;
(c) separating said solids from said solvent.

19. A method according to claim 18 wherein in said step (a) said solution is formed by separately forming a first solution comprising calcium and acetate ions and a second solution comprising calcium and magnesium ions and combining said solutions.

20. A method according to claim 18 wherein in said step (b) said solids are formed by cooling said solution whereby substantially pure calcium magnesium crystallizes from said solution.

21. A method according to claim 18 wherein said step (b) comprises removing a sufficient amount of water from said solution whereby substantially pure calcium magnesium acetate crystallizes from said solvent.

22. A method according to claim 19 wherein said step (b) comprises contacting said two solutions as sprays.

23. A method according to claim 18 wherein said step (b) comprises the step of atomizing said solution, whereupon said solids are formed.

24. A method of preparing calcium, magnesium and acetate solids comprising the steps of:
a) forming a solution comprising calcium, magnesium and acetate ions in a homogeneous solvent comprising at least 50% acetic acid, with the remaining being water; wherein the solubility of calcium magnesium acetate acetic acid is less than a solubility of either calcium acetate or magnesium acetate in acetic acid;
b) removing a sufficient amount of water from said solution whereby substantially pure calcium magnesium acetate crystallizes from said solvent;
c) separating said solids from said solvent.

25. A method according to claim 24 wherein said solvent comprises at least 80% acetic acid, with the remaining being water.

26. A method according to claim 24 wherein said solvent comprises at least 1 ml of water per gram of calcium acetate hemihydrate introduced into said solvent.

27. A method according to claim 25 wherein said solvent comprises at least 2 mls of water per gram of calcium acetate hemihydrate introduced into said solvent.

28. A method according to claim 24 whereby water is removed from said solution in step (b) by evaporation.

* * * * *